United States Patent [19]

Hahn et al.

[11] Patent Number: 4,542,521
[45] Date of Patent: Sep. 17, 1985

[54] RADIOGRAPHIC INSTALLATION FOR AN X-RAY EXAMINATION APPARATUS

[75] Inventors: Alfred Hahn, Erlangen; Werner Rauch, Nuremberg; Norbert Barthelmes, Erlangen, all of Fed. Rep. of Germany

[73] Assignee: Siemens Aktiengesellschaft, Berlin & Munich, Fed. Rep. of Germany

[21] Appl. No.: 514,702

[22] Filed: Jul. 18, 1983

[30] Foreign Application Priority Data

Sep. 29, 1982 [DE] Fed. Rep. of Germany ....... 3236081

[51] Int. Cl.$^4$ ................................................ A61B 6/00
[52] U.S. Cl. ..................................... 378/155; 378/154
[58] Field of Search ............... 378/154, 155, 160, 172, 378/173, 174, 175, 186

[56] References Cited

U.S. PATENT DOCUMENTS 3,763,370  9/1973  Hanson ................................. 378/172
4,105,920  8/1978  Pury et al. ........................... 378/155

FOREIGN PATENT DOCUMENTS 2921034  11/1980  Fed. Rep. of Germany ...... 378/154
1101892   3/1965  United Kingdom ................ 378/155

Primary Examiner—Alfred E. Smith
Assistant Examiner—Charles F. Wieland
Attorney, Agent, or Firm—Hill, Van Santen, Steadman & Simpson

[57] ABSTRACT

A radiographic installation for an x-ray examination apparatus has two antiscatter grids disposed in different planes at different distances from the focus of the radiation source and are alternately movable by a motor connected thereto through a drive train from a standby position outside of the radiation field into a position within the radiation field. The grids are maintained in the standby position by a permanently-acting bias force and are moved into the radiation field by the motor in opposition to this force. The drive train includes a belt having two cams disposed at the opposite ends thereof respectively associated with the antiscatter grids for limiting the movement thereof to define selected positions for the grids.

7 Claims, 1 Drawing Figure

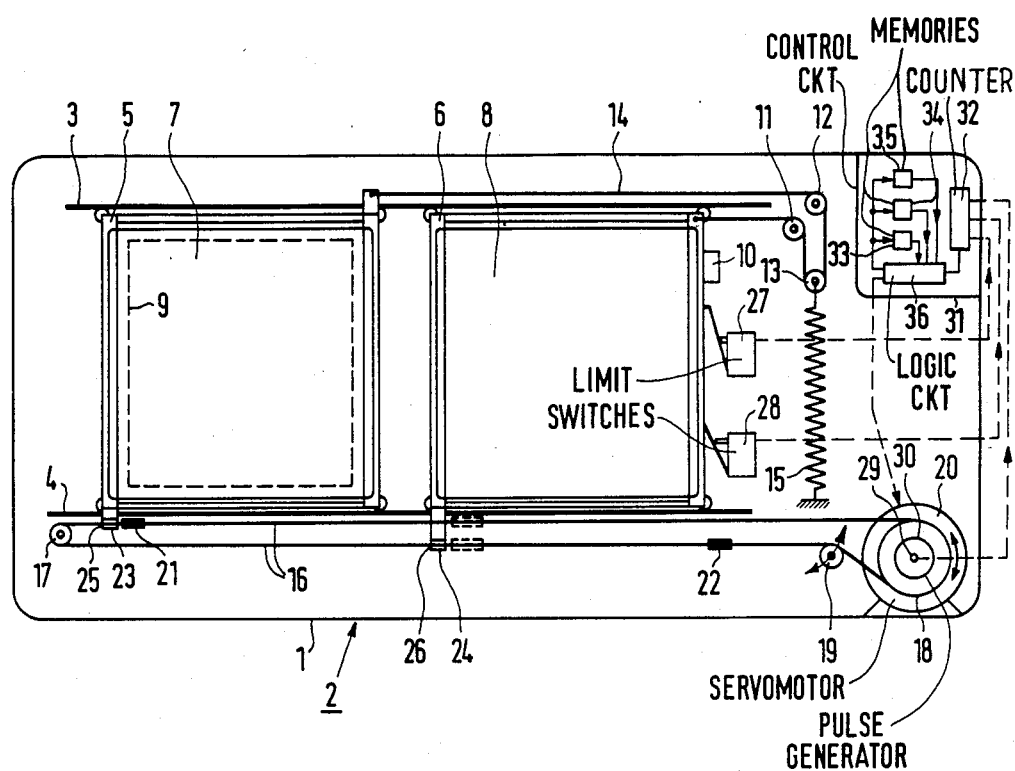

RADIOGRAPHIC INSTALLATION FOR AN X-RAY EXAMINATION APPARATUS

BACKGROUND OF THE INVENTION

1. Field of the Invention

The present invention relates to a radiographic installation for an x-ray examination apparatus, and in particular to such an installation having two antiscatter grids disposed in different planes at different differences from the focus of the radiation source which are alternately movable from a standby position outside of the radiation field to a position within the radiation field, and a means for adjusting the position of the grids.

2. Description of the Prior Art

An x-ray examination apparatus is described in German Utility Model No. 1,898,153 wherein the distance between the focus of the x-ray tube and the x-ray image layer can be altered for generating teleradiographs. In this device, the radiographic installation has two antiscatter grids which are focused to the two different film focus intervals associated with the apparatus. The antiscatter grids can be alternately transported from a standby position into a radiographic position, and back to the standby position, by a single servomotor by means of two manually adjustable clutches or couplings which are synchronously locked relative to one another. This regulating drive means is relatively complicated and expensive to manufacture.

SUMMARY OF THE INVENTION

It is an object of the present invention to provide a radiographic installation having two antiscatter grids disposed at different distances in different planes from the radiation focus and a regulating drive for the grids which is simple to operate and economical to manufacture.

Another object of the present invention is to provide such a radiographic installation which can be utilized to prepare radiographs utilizing small radiation fields, in which relatively little scattered radiation results, thus not requiring the use of an antiscatter grid.

The above objects are inventively achieved in a radiographic installation having two antiscatter grids disposed in different planes at different distances from the radiation focus which are maintained by a permanently acting force in a standby position, and which are alternately movable by a single motor-driven traction cable in opposition to the permanently acting force into the radiation field. This structure permits radiographs to be prepared utilizing either one of the two antiscatter grids, or without an antiscatter grid. Because of the stable end or limiting position of the antiscatter grids in the standby position, only a small number of relatively simple components are required to construct the installation.

In a further embodiment of the invention, the traction cable has two cams respectively disposed at the opposite ends of the cable, each cam being associated with one of the antiscatter grids. The cable passes through a bore connected to the grid however the cam has a greater diameter than that of the bore and thus automatically engages the particular grid with the cable so as to commence movement of the grid from a specific location with respect to the cable. As a consequence, the position of the two antiscatter grids is solely determined by the position of the cable line, thus significantly simplifying control of the grid positions.

In another embodiment of the invention, the cams on the cable line may be mounted at reciprocal distances such that one cam engages its associated antiscatter grid, disposed in the standby position, at only one position of the cable line, at which time the other cam is already out of engagement with the other antiscatter grid, which is also in the standby position. This ensures, dependent solely upon the position of the cable, that only one of the antiscatter grids, or no scattered ray grid, is positioned in the radiographic exposure position. It is thus not possible for both antiscatter grids to be accidentally simultaneously in the radiographic exposure position.

DESCRIPTION OF THE DRAWINGS

The single FIGURE is a plan view of a radiographic installation constructed in accordance with the principles of the present invention including a block diagram illustrating control circuitry associated therewith.

DESCRIPTION OF THE PREFERRED EMBODIMENTS

A radiographic installation for an x-ray examination apparatus is generally referenced at 2 in the drawing. The installation has a housing 1 in which two pairs of rails disposed in different parallel planes are disposed. The pairs of rails are in registry and only the top-most rails 3 and 4 are visible in the drawings. One pair of rails has a transport frame 5 carrying an antiscatter grid 7 movable therein, and the other pair of rails has a transport frame 6 carrying another antiscatter ray grid 8 movable therein. The antiscatter grids 7 and 8 are thus disposed in different planes at different distances from the focus of the radiaton source (not shown). The left antiscatter grid 7 in the drawing is disposed in the radiographic exposure position and the maximally definable radiographic exposure field 9 is indicated in dashed lines. The other scattered ray grid 8 is disposed in the drawing in a standby position situated to the right of the radiographic exposure position. In this standby position, the transport frame 6 abuts a limiting stop 10. The frames 5 and 6 are connected to the opposite ends of a traction cable 14, which is guided by two deflection rollers 11 and 12 and an idler roller 13. The idler roller 13 is permanently biased by a tension spring 15.

The transport frames 5 and 6 have respective extension arms 23 and 24 having respective bores 25 and 26 through which a continuous cable 16 is guided. The continuous cable 16 is also entrained around two deflection rollers 17 and 18 and an idler roller 19. The deflection roller 18 is driven by a servomotor 20. The continuous cable 16 carries two cams 21 and 22 thereon. The diameter of the cams 21 and 22 is greater than the diameter of the bores 25 and 26 in the extension arms 23 and 24. A pair of limit switches 27 and 28 are also disposed in the installation two having actuators in different planes respectively associated with the grids 7 and 8.

A pulse generator 30 is carried on the axle 29 of the servomotor 20 which supplies pulses, dependent upon the angle of rotation, to a pulse counter 32 contained in a control unit 31. The limit switches 27 and 28 are also connected to the counter 32. The control unit 31 also includes permanently pre-programmed memories 33, 34 and 35, which are activated by means of a select switch (not illustrated) for the antiscatter grids 7 and 8 and which, in combination with the output of the pulse generator 32, control the servomotor 20 through a logic circuit 36.

As described above, the transport frame 6 at the right of the drawings abuts a limiting stop 10. The frame 6 is maintained against the stop 10 by the spring-loaded traction cable 14. The other transport frame 5 is maintained in the radiographic exposure position, in opposition to the force of the spring loaded traction cable 14, by the cam 21 carried on the continuous cable 16, the cam 21 abutting the extension arm 23. The left scattered ray grid 7 is thus centered with respect to the maximally definable radiographic exposure field 9.

If a radiographic exposure without the use of a scattered ray grid is desired, or if a normal fluroscopy operation is selected, the servomotor 20 is connected for operation in the clockwise direction. The two cams 21 and 22 are moved to the position indicated in the drawing in dashed lines. The pulses generated by the pulse generator 30 during the motor run, which are proportional to the regulating distance covered, are supplied to the counter 32. The servomotor 20 is disconnected as soon as the output of the pulse counter 32 is equal to the signal stored in the memories 33, 34 and 35 activated by selection of the antiscatter grids 7 and 8. During operation of the servomotor 20, the left transport frame 5 is moved by the tension spring 15 and the traction cable 14 to the standby position limited by the stop 10. Both antiscatter grids 7 and 8 are at this point disposed in registry in the standby position. The pulse counter 32 is reset to zero by the limit switches 27 and 28, also disposed in the standby position, as soon as both antiscatter grids 7 and 8 abut the limiting stop 10. A constant initial count is thereby guaranteed.

If, during selection of the other antiscatter grid 8, the servomotor 20 is operated still further in the clockwise direction, the cam 22 moves from the position indicated in the broken lines in the drawing further to the left and engages the transport frame 6, disposed in the readiness position. As the continuous cable 16 continues to move, the antiscatter grid 8 is transported counter to the force of the tension spring 15 acting through the traction cable 14. Upon attainment of the proper radiographic exposure position the servomotor 20 is disconnected in the manner described above. If two different pulse numbers are pre-programmed for the radiographic exposure positions for the two antiscatter grids 7 and 8, raster obliteration can also be realized with the same units by switching between these two pulse numbers stored for the radiographic exposure position.

A single servomotor thus suffices not only to prepare radiographs with one or the other of the antiscatter grids, but also permits both antiscatter grids to be moved out of the radiographic exposure field for use of the installation with no antiscatter grid.

Although modifications and changes may be suggested by those skilled in the art it is the intention of the inventors to embody within the patent warranted hereon all changes and modifications as reasonably and properly come within the scope of their contribution to the art.

We claim as our invention:

1. A radiographic installation for an x-ray examination apparatus having a radiation field comprising:
    two antiscatter grids;
    means supporting said antiscatter grids in two substantially parallel planes and permitting lateral movement of said grids in said respective planes from a standby position outside of said radiation field to a position within said radiation field;
    bias means connected to each of said grids for permanently applying a force thereto urging said grids into said standby position; and
    drive means having a single cable engageable with each of said grids for displacing said grids counter to said force from said standby position to said position within said radiation field.

2. A radiographic installation as claimed in claim 1 wherein said cable carries two cams respectively movable for abutting said grids for displacing said grids as said cable moves.

3. A radiographic installation as claimed in claim 2 wherein said cams are carried on said cable at respective positions such that when one of said cams abuts one of said grids in the standby position, the other of said cams is already out of abutment with the other of said grids in the standby position.

4. A radiographic installation as claimed in claim 1 wherein said bias means comprises a second cable connected to each of said grids and entrained about a spring-loaded idler roller for generating said force.

5. A radiographic installation as claimed in claim 1 further comprising a limiting stop against which said grids abut in said standby position for defining an end of said standby position.

6. A radiographic installation as claimed in claim 1 wherein said drive means includes a servomotor connected to an angular pulse generator and wherein said radiographic installation further comprises control means for said servomotor including a pulse counter connected to said pulse generator, said contnol means disconnecting said servomotor upon attainment of a selected number of pulses in said counter.

7. A radiographic installation as claimed in claim 6 wherein said control means further includes a storage means for storing two different pulse numbers respectively associated with the respective positions of said grids within said radition field for controlling operation of said servomotor for displacing said grids counter to said force.

* * * * *